United States Patent [19]

Klein et al.

[11] Patent Number: 5,051,405

[45] Date of Patent: Sep. 24, 1991

[54] ANTI-THROMBOTIC PEPTIDES AND PSEUDOPEPTIDES

[75] Inventors: Scott I. Klein, Audubon; Bruce F. Molino, Hatfield; Mark Czekaj, Holland; Charles J. Gardner, Royersford, all of Pa.

[73] Assignee: Rhone-Poulenc Rorer Pharmaceuticals Inc., Fort Washington, Pa.

[21] Appl. No.: 419,305

[22] Filed: Oct. 10, 1989

[51] Int. Cl.$^5$ .............................................. A61K 67/00
[52] U.S. Cl. ....................................... 514/18; 514/19; 530/331
[58] Field of Search ...................... 514/18, 19; 530/331

[56] References Cited

U.S. PATENT DOCUMENTS 4,683,291  7/1987  Zimmerman et al. .

FOREIGN PATENT DOCUMENTS 0319506  12/1988  European Pat. Off. .
2608160  12/1986  France .

OTHER PUBLICATIONS

Pierschbacher, J. Biol. Chem., "Influence of Stereochemistry of the Sequence . . . ", pp. 17294–17298 (1987).
"Competition for Related by Nonidentical Binding Sites on the Glycoprotein IIb–IIIa Complex by Peptides Derived from Platelet Adhesive Proteins", Cell, vol. 48 (Mar.) 1987, pp. 867–873; Santoro et al.
"Inhibition of Platelet Adhesion to Fibronectin, Fibrinogen and von Willebrand Factor Substrates by a Synthetic Tetrapeptide Derived from the Cell-Binding Domain of Fibronectin", Blood, vol. 66, No. 4 (Oct.), 1985, pp. 946–952, Haverstick et al.
"Inhibition of Fibrinogen Binding to Human Platelets by the Tetrapeptide Glycyl–L–Prolyl–L–Arginyl–L–Proline", Plow et al., Proc. Natl. Acad. Sci., vol. 79 (Jun.) 1982, pp. 3711–3715.
"The Effect of Arg–Gly–Asp–Containing Peptides on Fibrinogen and von Willebrand Factor Binding to Platelets", Plow et al., Proc. Natl. Acad. Sci., vol. 82 *Dec.) 1985, pp. 8057–8061.

*Primary Examiner*—Lester L. Lee
*Assistant Examiner*—E. J. Kraus
*Attorney, Agent, or Firm*—Imre (Jim) Balogh; James A. Nicholson

[57] ABSTRACT

Disclosed are novel peptides and pseudopeptides and pharmaceutical compositions thereof containing certain amino acids and pharmaceutical compositions thereof that inhibit platelet aggregation and thrombus formation in mammalian blood.

7 Claims, No Drawings

ANTI-THROMBOTIC PEPTIDES AND PSEUDOPEPTIDES

BACKGROUND OF THE INVENTION

1. Field of the Invention

This invention relates to novel compounds having anti-thrombotic activity. More particularly, the invention relates to novel peptides and pseudopeptides that inhibit platelet aggregation and thrombus formation in mammalian blood thereby being useful in the prevention and treatment of thrombosis associated with certain disease states, such as, myocardial infarction, stroke, peripheral arterial disease and disseminated intravascular coagulation.

2. Description of the Prior Art

Haemostasis, the biochemistry of blood coagulation, is an extremely complex and as yet not completely understood phenomena whereby normal whole blood and body tissue spontaneously arrest bleeding from injured blood vessels. Effective haemostasis requires the combined activity of vascular, platelet and plasma factors as well as a controlling mechanism to prevent excessive clotting. Defects, deficiencies, or excesses of any of these components can lead to hemorrhagic or thrombotic consequences.

Platelet adhesion, spreading and aggregation on extracellular matrices are central events in thrombus formation. These events are mediated by a family of platelet adhesive glycoproteins, i.e., fibrinogen, fibronectin, and von Willebrand factor. Fibrinogen is a co-factor for platelet aggregation, fibronectin supports platelet attachments and spreading reactions, and von Willebrand factor is important in platelet attachment to and spreading on subendothelial matrices. The binding sites for fibrinogen, fibronectin and von Willebrand factor have been located on the platelet membrane glycoprotein complex IIb/IIIa.

Adhesive glycoprotein, like fibrinogen, do not bind with normal resting platelets. However, when a platelet is activated with an agonist such as thrombin or adenosine diphosphate, the platelet changes its shape, perhaps making the GPIIb/IIIa binding site accessible to fibrinogen. The novel molecules described in this invention may block the fibrinogen receptor, thus inhibiting platelet aggregation and subsequent thrombus formation. Pharmaceutical agents and/or compositions possessing such inhibiting effect may be provided for the prophylaxis and treatment of thrombogenic diseases, such as myocardial infarction, stroke, peripheral arterial disease and disseminated intravascular coagulation.

It has been observed that the presence of Arg-Gly-Asp (RGD) is necessary in fibrinogen, fibronectin and von Willebrand factor for their interaction with the cell surface receptor (Ruoslahti E., Pierschbacher, Cell 1986, 44, 517–18). Two other amino acid sequences also seem to take part in the platelet attachment function of fibrinogen, namely, the Gly-Pro-Arg sequence, and dodecapeptide, His-His-Leu-Gly-Gly-Ala-Lys-Gln-Ala-Gly-Asp-Val, sequence. Synthetic small peptides containing the RGD or dodecapeptide units show activity: they bind to the platelet receptor and competitively inhibit binding of fibrinogen, fibronectin and von Willebrand factor as well as inhibiting aggregation of activated platelets (Plow et al. Proc. Natl. Acad. Sci. U.S.A. 1985, 82, 8057–61; Ruggeri et al. Proc. Natl. Acad. Sci. U.S.A. 1986, 5708–12; Ginsberg et al. J. Biol. Chem. 1985, 260, 3931–36; and Gartner et al. J. Biol. Chem. 1987, 260, 11,891–94).

The present invention is directed to novel peptides and pseudopeptides that contain certain amino acids which inhibit platelet aggregation and consequent thrombus formation.

SUMMARY OF THE INVENTION

In accordance with the present invention, novel peptides and pseudopeptides are provided for the prophylaxis and/or treatment of thrombotic diseased states having the general formula:

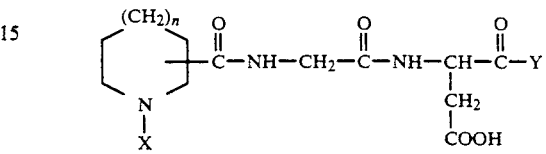

and pharmaceutically acceptable salts thereof, wherein:
X is H, amidino,

where R is alkyl, aryl or aralkyl;
Y is OH, OR$_1$ or
a naturally occurring L-amino acid bonded at the α-amino position selected from the group consisting of
Val
Ser
Gly
Ala
Tyr
Phe
Trp
Thr
Pro
Leu
Arg
Asn
Asp
Cys
Glu
His
Lys and
Met;
R$_1$ is alkyl, aryl, aralkyl or allyl; and
n is 0, 1 or 2.

As used herein: alkyl represents a saturated aliphatic hydrocarbon, either branched or straight chained, with up to 10 carbon atoms, and preferably up to 6 carbon atoms examples of which include methyl, ethyl, n-propyl, isopropyl, butyl, sec-butyl, t-butyl, amyl and hexyl; aryl preferably denotes phenyl and naphthyl; and aralkyl means an alkyl group substituted by an aryl radical, the preferred aralkyl groups being benzyl and phenethyl.

DETAILED DESCRIPTION OF THE INVENTION

In accordance with the present invention, novel compounds are provided which inhibit platelet aggregation by inhibiting fibrinogen binding to activated platelets and other adhesive glycoproteins involved in platelet aggregation and blood clotting. Compounds of the present invention, as tested by methods predictive of antithrombotic activity, are believed to be useful in the prevention and treatment of thrombosis associated with certain diseased states, such as myocardial infarction, stroke, peripheral arterial disease and disseminated intravascular coagulation.

The present compounds may also be useful for the treatment of certain cancerous diseases since they may interfere with adhesive interactions between cancer cells and the extracellular matrix (Journ. of Biol. Chem., Vol. 262, No. 36 1987, pp. 17703–17711; Science, Vol. 233, 1986, pp. 467–470; and Cell, Vol. 57, 59–69, Apr. 1989).

The compounds of the present invention may be readily prepared by standard solid phase or solution phase peptide synthesis techniques using starting materials and/or intermediates available from chemical supply companies such as Aldrich and Sigma or may be synthesized by standard organic chemical techniques. (H. Paulsen, G. Merz, V. Weichart, "Solid-Phase Synthesis of O-Glycopeptide Sequences", Angew. Chem. Int. Ed. Engl. 27 (1988); H. Mergler, R. Tanner, J. Gosteli, and P. Grogg, "Peptide Synthesis by a Combination of Solid-Phase and Solution Methods I: A New Very Acid-Labile Anchor Group for the Solid-Phase Synthesis of Fully Protected Fragments. Tetrahedron letters 29, 4005 (1988); Merrifield, R. B., "Solid Phase Synthesis After 25 Years: The Design and Synthesis of Antagonists of Glucagon", Makromol. Chem. Macromol. Symp. 19, 31 (1988).)

The solid phase method is represented schematically as follows:

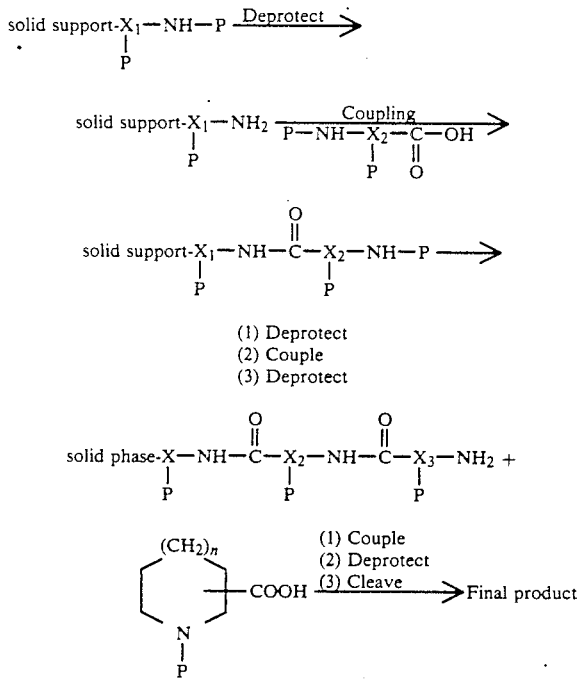

wherein: the solid support may be, but is not limited to, p-alkoxybenzyl alcohol resin,

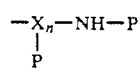

is a protected amino acid derivative and

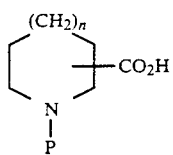

is a protected derivative of a nitrogen heterocycle carboxylic acid where n may be 0, 1 or 2.

In the synthetic process of making the desired compound the amino acid derivatives are added one at a time to the insoluble resin until the total sequence has been built up on the resin, then the heterocyclic derivative is coupled at the N-terminal of the chain. The functional groups of the amino acid derivatives and of the nitrogen heterocycle are protected by blocking groups to prevent cross reaction during the coupling procedure. These blocking groups include, but are not limited to, tertiary butoxy carbonyl (BOC), carbobenzoxy (CBZ), benzyl, t-butyl and 9-fluorenylmethoxy carbonyl (FMOC). Upon completion of each coupling reaction, the $\alpha$-amino protecting group is removed by standard procedures and, in turn, coupled to an amino acid derivative or heterocyclic derivative having a free carboxylic acid function. This procedure is repeated until the desired product derivative is formed. The final product is obtained by deprotection and cleavage of the product from the resin by standard techniques.

Alternatively, the compounds of the present invention may be prepared in solution, i.e., without using a solid support. In a manner that is similar to the solid phase synthesis, the protected amino acid or heterocyclic derivatives are coupled, then deprotected, using standard procedures.

The invention will now be explained further by the following illustrative examples:

EXAMPLE 1

1-Amidinopiperidine-4-Carboxylglycyl-L-Aspartyl-L-Valine

A. 0.26 g of N-(9-fluorenylmethoxycarbonyl)-L-valine p-alkoxybenzyl alcohol resin ester (containing 0.15 mmol of amino acid) was deprotected by shaking with 5 ml of 20% piperidine in dimethylformamide at room temperature for 1 hour. The mixture was filtered and the resin washed with methylene chloride to give L-valine p-alkoxybenzyl alcohol resin ester.

B. The product in Example 1A was shaken with 0.246 g N-FMOC-L-aspartic acid $\beta$-t-butyl ester, 0.115 g 1-(3-dimethylaminopropyl)-3-ethylcarbodiimide hydrochloride (EDC), 0.081 g 1-hydroxybenzotriazole (HOBT) and 0.08 ml triethylamine in 5 ml dimethylformamide for 1 hour. The resulting product was deprotected as in Example 1A to give L-aspartyl-$\beta$-t-butyl ester valine p-alkoxybenzyl alcohol resin ester.

C. The product from Example 1B was treated with 0.178 g N-FMOC-glycine in the presence of EDC, HOBT and triethylamine in dimethylformamide as in Example 1B, then deprotected as in Example 1A to give glycyl-L-aspartyl-$\beta$-t-butyl ester valine p-alkoxybenzyl alcohol resin ester.

D. To a solution of 1 g of isonipecotic acid in 10 ml of water was added 1.07 g potassium carbonate and this was stirred for 15 minutes at room temperature. 0.961 g aminoiminomethanesulfonic acid was then added portionwise over 20 minutes. The solution was stirred for 2 hours at room temperature, concentrated in vacuo to one-half of the original volume and the resulting precipitate collected by filtration. The resulting solid was recrystallized from water to give N-amidino-4-piperidine carboxylic acid.

E. The product from Example 1D was dissolved in an aqueous solution of tetrahydrofuran. To this solution was added one equivalent of 1N hydrogen chloride in ether. The resulting mixture was concentrated in vacuo to give N-amidino-4-piperidine carboxylic acid hydrochloride.

F. 0.063 mg N-amidino-4-piperidine carboxylic acid hydrochloride and the product from Example 1C were shaken together in 5 ml dimethylformamide in the presence of 0.057 g EDC, 0.040 g HOBT and 0.04 ml of triethylamine for 18 hours. The resulting product was cleaved from the resin, and the β-t-butyl protecting group removed by treating with 95% aqueous trifluoroacetic acid for 2 hours. The resin was removed by filtration and the filtrate was diluted with 0.5N aqueous acetic acid. Then the diluted filtrate was washed with ethyl acetate and lyophillized to give 1-amidinopiperidine-4-carboxyglycyl-L-aspartyl-L-valine as the trifluoroacetate salt. The salt decomposed at 140° C.

EXAMPLE 2

N-Amidino-3-Carboxylglycyl-L-Aspartyl-L-Valine

A. 2.5 g nipecotic acid was stirred with a solution of 2.67 g potassium carbonate in 20 ml of water to give a clear solution. To this solution was added 2.4 g aminoiminomethanesulfonic acid in small portions over a period of 10 minutes. The solution was allowed to stand overnight and the resulting precipitate recrystallized from water to give N-amidino-piperidine-3-carboxylic acid.

B. The product from Example 2A was treated as in Example 1E to give N-amidino-3-piperidine carboxylic acid hydrochloride.

C. Glycyl-L-aspartyl-β-t-butyl ester valine p-alkoxybenzyl alcohol resin ester, prepared as in Example 1C was treated with N-amidino-3-piperidine carboxylic acid hydrochloride in a manner similar to that of Example 1F to give N-amidinopiperidine-3-carboxylglycyl-L-aspartyl-L-valine as the trifluoroacetate salt; m.p. 53°–55° C.

EXAMPLE 3

Piperidine-3-Carboxylglycyl-L-Aspartyl-L-Valine

A. 1.29 g nipecotic acid and 2.76 g potassium carbonate were combined in 100 ml of 50% aqueous tetrahydrofuran and 2.18 g di-t-butyl dicarbonate was added. The mixture was stirred vigorously for 17 hours. The mixture was evaporated in vacuo to remove the tetrahydrofuran, then acidified with 1N hydrochloric acid and the mixture extracted with ethyl acetate. The ethyl acetate solution was dried over sodium sulfate, filtered and evaporated to give N-t-butoxycarbonylpiperidine-3-carboxylic acid.

B. The product from Example 3A and glycyl-L-aspartyl-β-t-butyl ester valine-p-alkoxybenzyl alcohol resin ester were treated as in Example 1F. The product so obtained was deprotected with trifluoroacetic acid as in Example 1F resulting in the removal of the N-t-butoxycarbonyl protecting group as well as the β-t-butyl protecting group and the cleavage of the product from the resin to give N-amidino-3-carboxylglycyl-L-aspartyl-L-valine as the trifluoroacetate salt; m.p. 49°–50° C.

EXAMPLE 4

Piperidine-4-carboxylglycyl-L-Aspartyl-L-Valine

A. Isonipecotic acid was treated as in Example 3A to give N-t-butoxycarbonyl-piperidine-4-carboxylic acid.

B. The product from Example 4A was treated in a manner similar to that in Example 3B to give piperidine-4-carboxylglycyl-L-aspartyl-L-valine as the trifluoroacetate salt; m.p. 79°–81° C.

Compounds of the present invention were tested for inhibition of platelet aggregation using the following procedures:

I. Inhibition of Radiolabeled ($^{125}$I) Fibrinogen Binding Assay, which is essentially based on the method described in Proc. Natl. Acad. Sci. U.S.A. Vol. 83, pp. 5708–5712, August 1986, and is as follows.

Platelets are washed free of plasma constituents by the albumin density-gradient technique. In each experimental mixture platelets in modified Tyrode's buffer are stimulated with human α-thrombin at 22°–25° C. for 10 minutes ($3.125 \times 10''$ platelets per liter and thrombin at 01 N1H units/ml). Hirudin is then added at a 25-fold excess for 5 minutes before addition of the radiolabeled ligand and any competing ligand. After these additions, the final platelet count in the mixture is $1 \times 10''$/liter. After incubation for an additional 30 minutes at 22°–25° C., bound and free ligand are separated by centrifuging 50 μl of the mixture through 300 μl of 20% sucrose at 12,000 xg for 4 minutes. The platelet pellet is then separated from the rest of the mixture to determine platelet-bound radioactivity. Nonspecific binding is measured in mixtures containing an excess of unlabeled ligand. When binding curves are analyzed by Scatchard analysis, nonspecific binding is derived as a fitted parameter from the binding isotherm by means of a computerized program. To determine the concentration of each inhibitory compound necessary to inhibit 50% of fibrinogen binding to thrombin-stimulated platelets ($IC_{50}$), each compound is tested at 6 or more concentrations with $^{125}$I-labeled fibrinogen held at 0.176 μmol/liter (60 μg/ml). The $IC_{50}$ is derived by plotting residual fibrinogen binding against the logarithm of the sample compound's concentration.

II. Inhibition of Fibrinogen - Mediated Platelet Aggregation, which is essentially based on the method described in Blood, Vol. 66, No. 4, Oct. 1985, pp. 946–952, and is as follows.

Human Platelets were isolated from freshly drawn whole blood and were suspended in 0.14 mol/L NaCl, 2.7 mmol/L Kll, 12 mmol/L NaHCO$_3$, 0.42 mmol/L Na$_2$HPO$_4$, 0.55 mmol/L glucose, and 5 mmol/L Hepes, pH 7.35 at $2 \times 10^8$ platelets/ml. The suspension was incubated at 37° C. An aliquot of 0.4 ml of platelet suspension was activated by human thrombin at a final concentration of 2 μg/ml of thrombin for one minute. After one minute the reaction was stopped by a thrombin inhibitor. Serial dilution of the compound being tested was then added to the activated platelet, the reaction was allowed to proceed for one minute, followed by the addition of human fibrinogen at a final concentration of 60 μ/ml of fibrinogen. Platelet aggregation was then recorded by an aggregometer. Rate of aggregation was used to calculate $IC_{50}$.

Representative results of platelet aggregation inhibition are shown in Table I.

TABLE I

| | Inhibition of $^{125}$I-Fibrinogen Binding to Platelets IC$_{50}$(μM) | Inhibition of Fibrinogen Mediated Platelet Aggregation | |
|---|---|---|---|
| | | IC$_{50}$(μM) | % Inhibition at 100 μM |
| Piperidine-4-carboxylglycyl-L-aspartyl-L-valine | 10.5 | 6.0 | 86 |
| 1-Amidinopiperidine-4-carboxylglycyl-L-aspartyl-L-valine | 1.8 | 3.4 | 92 |
| Piperidine-3-carboxylglycyl-L-aspartyl-L-valine | >64 | 52 | 78 |
| 1-Amidinopiperidine-3-carboxylglycyl-L-aspartyl-L-valine | 10.5 | 9.1 | 87 |

The compounds of the present invention may be orally or parenterally administered to mammals. The compound may be incorporated into pharmaceutical formulations having excipients suitable for these administrations and which do not adversely react with the compounds, for example, water, vegetable oils, certain alcohols and carbohydrates, gelatin and magnesium stearate. The pharmaceutical formulations containing an active compound of the present invention may be made into: tablets, capsules, elixirs, drops or suppositories for enteral administration; and solutions, suspensions or emulsions for parenteral administration.

In general, compound of this invention is administered in dosages of approximately 1 to 200 mg per dosage unit or higher. The daily dosage is approximately 0.02-5 mg/kg of body weight. It is to be understood, however, that the particular dose for each patient as usually depends on very diverse factors, such as the age, body weight, general condition of health, sex, diet and the like of the patient, on the time and route of administration, on the rate of excretion, on the combination of medicaments and on the severity of the disease.

Having described the invention, it will be apparent to one of ordinary skill in the art that changes and modifications can be made thereto without departing from the spirit and scope of the invention as set forth herein.

What is claimed is:

1. A compound of the formula

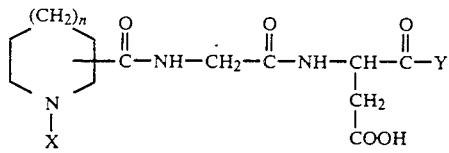

and pharmaceutically acceptable salts thereof, wherein:
X is H, amidino,

where R is alkyl, aryl or aralkyl;
Y is OH, OR$_1$ or a naturally occurring L-amino acid bonded at the α-amino position selected from the group consisting of
Val
Ser
Gly
Ala
Tyr
Phe
Trp
Thr
Pro
Leu
Arg
Asn
Asp
Cys
Glu
His
Lys and
Met;
R$_1$ is alkyl, aryl, aralkyl or allyl; and
n is 0, 1 or 2.

2. A pharmaceutical composition for the prophylaxis of abnormal thrombus formation in a mammal comprising a pharmaceutically acceptable carrier and a pharmaceutically effective amount of a compound of claim 1.

3. A method of preventing thrombus formation in a mammal comprising the administration of the composition of claim 2.

4. Piperidine-4-carboxylglycyl-L-aspartyl-L-valine.

5. 1-Amidinopiperidine-4-carboxylglycyl-L-aspartyl-L-valine.

6. Piperidine-3-carboxylglycyl-L-aspartyl-L-valine.

7. 1-Amidinopiperidine-3-carboxylglycyl-L-aspartyl-L-valine.

* * * * *